United States Patent
Wang et al.

(10) Patent No.: US 12,077,781 B2
(45) Date of Patent: Sep. 3, 2024

(54) CARDIOMYOCYTE PREPARATION AND PREPARATION METHOD THEREFOR AND USE THEREOF

(71) Applicant: HELP STEM CELL INNOVATIONS CO., LTD., Suzhou (CN)

(72) Inventors: Jiaxian Wang, Suzhou (CN); Qian Wang, Suzhou (CN); Yat Ping Tsui, Suzhou (CN); Xiao Xu, Suzhou (CN)

(73) Assignee: HELP STEM CELL INNOVATIONS CO., LTD., Jiangsu (CN)

( * ) Notice: Subject to any disclaimer, the term of this patent is extended or adjusted under 35 U.S.C. 154(b) by 973 days.

(21) Appl. No.: 17/043,270

(22) PCT Filed: Dec. 19, 2019

(86) PCT No.: PCT/CN2019/126486
§ 371 (c)(1),
(2) Date: Sep. 29, 2020

(87) PCT Pub. No.: WO2020/135199
PCT Pub. Date: Jul. 2, 2020

(65) Prior Publication Data
US 2021/0009957 A1   Jan. 14, 2021

(30) Foreign Application Priority Data
Dec. 29, 2018   (CN) .......................... 201811642451.X

(51) Int. Cl.
| | | |
|---|---|---|
| *C12N 5/077* | (2010.01) | |
| *A61K 9/00* | (2006.01) | |
| *A61K 35/33* | (2015.01) | |
| *A61K 35/34* | (2015.01) | |
| *A61P 9/00* | (2006.01) | |

(52) U.S. Cl.
CPC .......... *C12N 5/0657* (2013.01); *A61K 9/0019* (2013.01); *A61K 35/33* (2013.01); *A61K 35/34* (2013.01); *A61P 9/00* (2018.01); *C12N 5/0656* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | |
|---|---|---|
| 2003/0031651 A1 | 2/2003 | Lee et al. |
| 2006/0104961 A1 | 5/2006 | Law |
| 2007/0258948 A1* | 11/2007 | Kolossov .............. A61K 35/44 435/6.13 |
| 2014/0094388 A1* | 4/2014 | Wakatsuki ........ G01N 33/5082 435/6.13 |
| 2015/0299658 A1 | 10/2015 | Ma |
| 2018/0153155 A1 | 6/2018 | Ohashi et al. |

FOREIGN PATENT DOCUMENTS

| | | |
|---|---|---|
| CN | 1533431 A | 9/2004 |
| CN | 1688701 A | 10/2005 |
| CN | 107460164 A | 12/2017 |
| CN | 109589337 A | 4/2019 |
| EP | 3476395 A1 | 1/2019 |
| WO | 03006950 A2 | 1/2003 |
| WO | 2017010544 A1 | 1/2017 |
| WO | 2018155651 A1 | 8/2018 |

OTHER PUBLICATIONS

Ban et al., Theranostics, 2017, vol. 7, issue 7, pp. 2067-2077. (Year: 2017).*
Tohyama et al., Cell Metabolism, 2016, col. 23, pp. 663-674. (Year: 2016).*
JPO Notice of Reasons for Refusal for corresponding JP Application No. 2021-517103; Issued on Nov. 30, 2021.
International Search Report for International Application No. PCT/CN2019/126486; Mailing date, Mar. 25, 2020.
Laflamme et al. "Cardiomyocytes derived from human embryonic stem cells in pro-survival factors enhance function of infarcted at hearts." Nature Biotechnology, vol. 25, No. 9, Aug. 26, 2007, pp. 1015-1024.
EPO Extended European Search Report for corresponding EP Application No. 19904186.4; Issued on Sep. 29, 2022.
Moore-Morris et al., "Cardiac fibroblasts: from development to heart failure", J Mol Med, Jul. 2015, 8 pages.
Qiu et al., "Rapamycin and CHIR99021 Coordinate Robust Cardiomyocyte Differentiation from Human Pluripotent Stem Cells via Reducing p53-Dependent Apoptosis", Key Laboratory of Stem Cell Biology, Institute of Health Sciences, Jun. 7, 2017, 29 pages.
Rajala et al., "Cardiac Differentiation of Pluripotent Stem Cells", Stem Cells International, Feb. 2011, 12 pages.
Wang et al., "GSK 3 B Inhibitor CHIR-99021 Promotes Proliferation through Upregulating B-Catenin in Neonatal Atrial Human Cardiomyocytes", J Cardiovasc Pharmacol, vol. 68, No. 6, Dec. 2016, 8 pages.

* cited by examiner

*Primary Examiner* — Allison M Fox
(74) *Attorney, Agent, or Firm* — CANTOR COLBURN LLP

(57) ABSTRACT

Provided are a cardiomyocyte preparation, a preparation method therefor and the use of the preparation in treating heart failure. The cardiomyocyte preparation comprises cardiomyocytes and fibroblasts, differentiated from pluripotent stem cells, wherein the concentration of the cardiomyocytes in the cardiomyocyte preparation is $0.75 \times 10^7$-$1.0 \times 10^9$ cells/mL, and the content of the cardiomyocytes is higher than 80% while the content of the fibroblasts is not higher than 20%. The cardiomyocyte preparation can improve cardiac ejection fraction and left ventricular fractional shortening, and increase the thickness of the left ventricular inner wall.

10 Claims, 3 Drawing Sheets

CARDIOMYOCYTE PREPARATION AND PREPARATION METHOD THEREFOR AND USE THEREOF

CROSS REFERENCE TO RELATED APPLICATIONS

This is the U.S. national stage of application No. PCT/CN2019/126486, filed on Dec. 19, 2019. Priority under 35 U.S.C. § 119(a) and 35 U.S.C. § 365 (b) is claimed from Chinese Application No. 201811642451.X, filed Dec. 29, 2018, the disclosure of which is also incorporated herein by reference.

FIELD

The present disclosure relates to the technical field of cell preparations, in particular to a cardiomyocyte formulation, preparation method therefor and uses thereof.

BACKGROUND

Heart failure is a pathological phenomenon of cardiac insufficiency caused by the development of various heart diseases to the late stage. It is a group of clinical syndromes in which the ventricular filling or ejection ability is impaired due to disorders of the systolic or diastolic function of the heart. The clinical manifestations include a decrease in ejection fraction and short-axis fractional shortening of the ventricle, an increase in myocardial wall pressure, an increase in the diameter of the heart cavity, and an increase in the volume of the left ventricle during diastole and systole.

American College of Cardiology/American Heart Association (ACC/AHA) divides heart failure into four stages: A, B, C, and D. Stages A and B refer to patients who lack early symptoms of heart failure, but there are risk factors or have heart abnormalities, and these abnormalities include changes in the shape and structure of the heart; stage C refers to patients who have current or past symptoms of heart failure, such as shortness of breath, etc.; stage D is the severe stage of heart failure, called end-stage heart failure or refractory heart failure.

The epidemiological survey of heart failure in China shows that the current incidence of heart failure is 0.7% in men and 1% in women. With the increase of age, the incidence of heart failure gradually increases. If heart failure occurs, the patient will form a vicious circle, which is also a disease with a very high mortality rate in the elderly. With the aging of Chinese society getting worse, heart failure will become one of the reasons that seriously endanger the physical fitness of people.

The current therapies of treating heart failure mainly use chemical drugs to treat heart failure by reducing the activity of the neuroendocrine system, blocking or improving the adverse effects caused by the overexcitement of AT1R, or eliminating water and sodium retention during heart failure. However, clinical practice shows that these chemical drugs have different adverse reactions in the treatment of heart failure, such as hypotension or deterioration of renal function.

With the development of stem cell technology, researchers in this field are committed to studying how to treat end-stage heart failure caused by various heart diseases through stem cell transplantation. However, at present, the effect of these programs on the improvement of heart function is not obvious, and subsequent safety studies have found that the injected stem cells in the body are tumorigenic, which makes it not suitable for clinical research and treatment.

SUMMARY

In view of above, one aspect of the present disclosure is to provide a safe and reliable cardiomyocyte formulation that can effectively enhance the cardiac function of patients with heart failure, wherein the cardiomyocyte formulation comprises cardiomyocytes and fibroblasts differentiated from pluripotent stem cells, and the concentration of the cardiomyocytes in the cardiomyocyte formulation is $0.75 \times 10^7$ to $1.0 \times 10^9$ cells/mL, and the content of the cardiomyocytes is higher than 80% and the content of the fibroblasts is not higher than 20%.

The cardiomyocytes may be cardiomyocytes directly differentiated from pluripotent stem cells, or they may be cardiomyocytes resuscitated by cryopreservation.

In the cardiomyocyte formulation provided by the present disclosure, the concentration of cardiomyocytes is defined to $0.75 \times 10^7$ to $1.0 \times 10^9$ cells/mL. This concentration can not only improve the viability of cells in the cardiomyocyte formulation, but also enable the cardiomyocyte formulation to effectively improve the ejection fraction and left ventricular shortening fraction, increase the thickness of the ventricular wall and improve heart function in patients with heart failure. In addition, through a large number of experiments, the inventors of the present disclosure found that the cardiomyocyte formulation containing a certain amount of fibroblasts helps to improve the cardiac function of patients with heart failure. When the content of fibroblasts in the cardiomyocyte formulation is not higher than 20%, the cardiomyocyte formulation can effectively increase the ejection fraction of the heart; when the content of fibroblasts is higher than 20%, the improvement of the ejection fraction is not obvious and even decreased with the increase of the content of fibroblasts.

Since the content of cardiomyocytes in the cardiomyocyte formulation is defined to more than 80% in the examples of the present disclosure, the content of pluripotent stem cells in the cardiomyocyte formulation is reduced to a certain extent, which reduces the tumorigenicity of pluripotent stem cells and ensures that the cardiomyocyte formulation can improve the heart function of patients with heart failure and also improve the safety of the preparations at the same time.

Preferably, in the cardiomyocyte formulation, the concentration of the cardiomyocytes is $0.5 \times 10^8$ to $1.2 \times 10^8$ cells/mL. When the concentration of cardiomyocytes in the cardiomyocyte formulation is within this range, the cardiomyocyte formulation has a better effect of improving the cardiac function of patients with heart failure.

Preferably, the residual amount of pluripotent stem cells in the cardiomyocyte formulation is not more than 1%. Specifically, the content of Nanog, SSea4 and Oct3/4 positive cells in the cardiomyocyte formulation is not more than 1%.

The examples of the present disclosure show that cardiomyocyte formulation with a residual amount of pluripotent stem cells exceeding 30% might be tumorigenic. In order to eliminate the hidden safety hazards in the use of cardiomyocyte formulations, according to a large number of in vitro and in vivo experimental data, the content of pluripotent stem cells in the cardiomyocyte formulation is controlled within 1%, which can effectively eliminate the tumorigenicity of the cardiomyocyte formulation.

Further preferably, the residual amount of pluripotent stem cells in the cardiomyocyte formulation is not more than 0.3%, specifically, the content of Nanog, SSea4, and Oct3/Oct4 positive cells in the cardiomyocyte formulation is not more than 0.3%.

On the other hand, the present disclosure provides a method for preparing the cardiomyocyte formulation, wherein the cardiomyocytes are prepared from pluripotent stem cells through the following steps:

1) pretreating pluripotent stem cells: seeding the pluripotent stem cells into a pluripotent stem cell culturing medium at a density of $0.9 \times 10^5$ to $3.0 \times 10^5$ cells/cm$^2$, culturing the cells at 37° C. with 5% $CO_2$ until cell density exceeds 40%;
2) differentiating to cardiomyocytes: removing the pluripotent stem cell culture medium by suction, adding cardiomyocyte differentiation medium containing 0.01 to 0.09 mM CHIR99021, culturing for 48 hours; replacing the medium to cardiomyocyte differentiation medium containing 0.01 to 0.05 mM IWR-1, continuing to culture the cells for 48 hours; continuing to culturing with the cardiomyocyte differentiation medium, and replacing the cardiomyocyte differentiation medium according to the cell growth state; and
3) purifying cardiomyocytes: continuing to culture the cardiomyocytes in the step of differentiating to cardiomyocytes until emergence of observable beating, seeding the cells in the cardiomyocyte differentiation medium at a density of $6.0 \times 10^5$ to $9.0 \times 10^5$ cells/cm$^2$, and adjusting the content of fibroblasts to less than 20% by using a cardiomyocyte purification liquid.

Preferably, in the method for preparing the cardiomyocyte formulation, the pluripotent stem cells include induced pluripotent stem cells and embryonic stem cells.

Further preferably, in the method for preparing the cardiomyocyte formulation, the step of purifying cardiomyocytes further comprises culturing the cells in a cardiomyocyte culturing medium containing 0.75-5 μM STF-31 for 2-5 days. STF-31 can remove undifferentiated pluripotent stem cells in the step of differentiating to cardiomyocytes and improve the purity of cardiomyocytes. By changing the concentration of STF-31 or purification time, the content of pluripotent stem cells in the preparation can be controlled.

More preferably, the method for preparing the cardiomyocyte formulation further comprises preparing a cell suspension with a cardiomyocyte concentration of $0.75 \times 10^7$ to $1.0 \times 10^9$ cells/mL by using the cells obtained in the step of purifying cardiomyocytes and physiological saline under sterile conditions.

After the contents of cardiomyocytes, pluripotent stem cells and fibroblasts in the cardiomyocyte formulation prepared from pluripotent stem cells are detected, physiological saline can be added according to actual needs to control the concentration of cardiomyocytes.

In another aspect, the present disclosure provides use of the cardiomyocyte formulation in the manufacture of a medicament for treating heart failure.

Preferably, in the use of the cardiomyocyte formulation in the manufacture of a medicament for treating heart failure, the cardiomyocyte formulation is used to treat heart failure with reduced ejection fraction (HFrEF). The cardiomyocyte formulations provided by the examples of the present disclosure have better effect on improving the cardiac function of patients with HFrEF heart failure than the effect on patients with HFpEF heart failure.

Preferably, in the use of the cardiomyocyte formulation in the manufacture of a medicament for treating heart failure, the cardiomyocyte formulation is injected through epicardium via a syringe into a scar or a thinned myocardial wall region.

The cardiomyocyte formulations provided by the present disclosure have the following beneficial effects: the cardiomyocyte formulations within the concentration range provided by the present disclosure can effectively alleviate the decrease in cardiac ejection fraction of patients with heart failure, increase the left ventricular shortening fraction, increase the thickness of the ventricular wall, and improve the heart functions; the cardiomyocyte formulation does not have the risk of tumorigenesis; the preparation methods of the cardiomyocyte formulation provided by the present disclosure are simple, highly repeatable and suitable for large-scale production.

Figure 1:
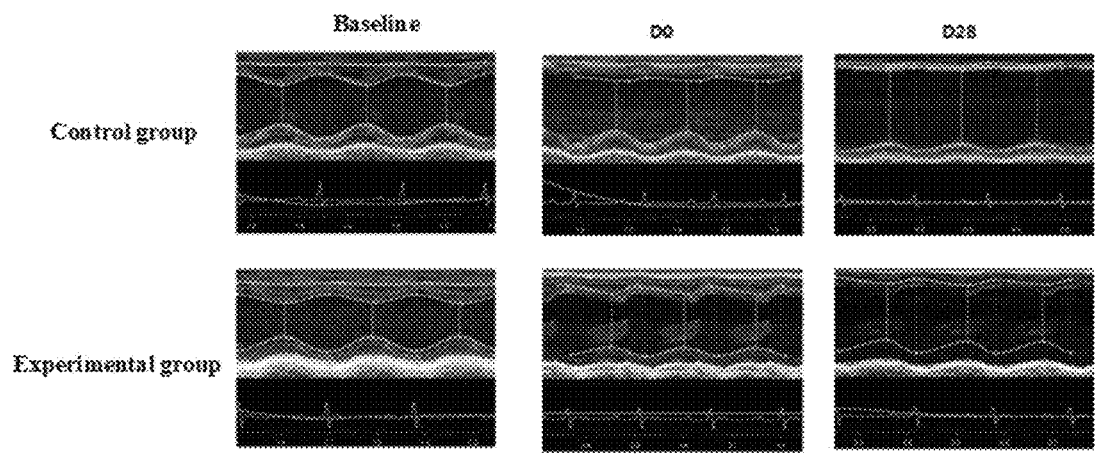
FIG. 1 shows the left ventricular short axis M-mode ultrasound results of the control group and the experimental group before the establishment of the heart failure model (baseline), D0 and D28, respectively, in Example 3. In the control group (heart failure model), the anterior wall of the left ventricle became thinner over time; while the thickness of the left ventricular anterior wall of the experimental group at D28 was greater than that of the control group at D28.

Wherein, the baseline described in the examples of the present disclosure is the state of the rat cardiac functions before heart failure modeling, which reflects the normal state of the rat cardiac functions.

D0 is the data of the heart failure model before the injection in the control group or the experimental group, which reflects the heart functions of the heart failure model rats.

D28 is the data 28 days after the injection in the control group or the experimental group with heart failure, which reflects the heart functions of the heart failure model rats, and combined with the data of D0 can be used to evaluate the changes in the heart functions of the heart failure model.

DETAILED DESCRIPTION

Unless defined otherwise, all technical and scientific terms used herein have the same meaning as commonly understood by those of ordinary skill in the art to which the embodiments belong. The terms used herein are used to describe specific examples and are not intended to limit the present disclosure.

In order to understand the present disclosure more clearly, the following terms are defined:

Pluripotent stem cell culture medium refers to the culture medium used to culture and amplify pluripotent stem cells (including induced pluripotent stem cells and embryonic stem cells). In the initial culturing conditions of pluripotent stem cells, gelatin was needed to coat the surface, mouse embryonic fibroblasts (MEF) were needed as feeder layer, and the traditional medium also used complex knockout serum replacement (KOSR) as main additives. With the continuous optimization of culturing conditions, some basic media and additives are combined to culture pluripotent stem cells. The basic medium includes but not limited to DMEM/F12, and other medium containing a certain concentration of glucose and essential amino acids required for the growth of stem cells can also be used as a basic medium. Additives include but not limited to sodium bicarbonate, recombinant human basic fibroblast growth factor, recombinant human lactoferrin, insulin, ascorbic acid, recombinant human transforming growth factor and the like. The pluripotent stem cell culture medium used in the examples of the present disclosure is not limited to the above-mentioned various culture media, and all the culture medium known to those skilled in the art that can be used to culture pluripotent stem cells should be included in the protection scope of the present disclosure.

Cardiomyocyte medium refers to a culture medium used to provide nutrition to cardiomyocytes and maintain the function of cardiomyocytes.

In the present disclosure, cardiomyocytes refer to cells differentiated from pluripotent stem cells and specifically express cardiac troponin T (cTnT).

In the present disclosure, the residual amount of pluripotent stem cells refers to the percentage of undifferentiated pluripotent stem cells in the cell products differentiated from pluripotent stem cells into cardiomyocytes.

Ejection fraction (EF) refers to the ratio of ventricular output per stroke to ventricular end-diastolic volume. It reflects the ejection function of the ventricle from the perspective of volume, and can be checked by cardiac color Doppler ultrasound. The ejection fraction is related to the contractility of the myocardium. The stronger the myocardial contractility, the greater the ejection fraction.

In the examples of the present disclosure, the cardiac function status (ejection fraction as the evaluation index) of each heart failure model mouse is not completely the same when the cardiomyocyte formulation is injected. In order to objectively evaluate the effect of cardiomyocyte formulation on cardiac function, the concept of change of ejection fraction is introduced:

$$\text{Change of EF} = \text{EF}_{(after\ treatment\ with\ cardiomyocyte\ formulation)} - \text{EF}_{(before\ injection\ of\ cardiomyocyte\ formulation)}$$

HFrEF refers to heart failure with reduced ejection fraction. Patients with this type of heart failure are based on physical signs and left ventricular ejection fraction (LVEF) as the main diagnostic indicators, and the LVEF≤40.

HFpEF refers to heart failure with preserved ejection fraction. This type of heart failure has impaired left ventricular diastolic active relaxation and reduced myocardial compliance, resulting in impaired left ventricular diastolic filling, reduced heart rate, and left ventricular end diastolic pressure increased, thus appearing symptoms and signs of heart failure. Left ventricular ejection fraction (LVEF) is roughly normal, with LVEF≥50.

The specific embodiments of the present disclosure are further described below in conjunction with the accompanying drawings of the specification. However, the present disclosure may be embodied in different forms and should not be construed as being limited to the examples set forth herein. These examples are provided only to make the present disclosure more complete and convey the scope of the present disclosure to those skilled in the art.

1. Method of Preparing Cardiomyocyte Formulation

1) Method for Differentiating Pluripotent Stem Cells into Cardiomyocytes

Step of pluripotent stem cell pretreatment: Embryonic stem cells (ESC) or induced pluripotent stem cells (iPSC) were seeded into pluripotent stem cell culturing medium at $0.9 \times 10^5$ cells/cm$^2$, $1.5 \times 10^5$ cells/cm$^2$, and $3.0 \times 10^5$ cells/cm$^2$, respectively, and cultured at 37° C. with 5% $CO_2$ until the density exceeded 40%. The pluripotent stem cell culture medium was TeSR™-E8™ medium. The seeding density of pluripotent stem cells affects the growth rate of pluripotent stem cells. In order to improve the differentiation efficiency of pluripotent stem cells on the whole, in the examples of the present disclosure, the seeding density was $0.9 \times 10^5$ to $3.0 \times 10^5$.

The pluripotent stem cell culture medium may also be a DMEM/F12 medium with adding an appropriate amount of recombinant human insulin, recombinant transferrin, human albumin, ferric citrate, bFGF, EGF, TGF-β, L-ascorbic acid and β-mercaptoethanol to establish an environment suitable for the growth of pluripotent stem cells.

Step of cardiomyocyte differentiation: When the pluripotent stem cell density exceeded 40%, the pluripotent stem cell culture medium was removed by suction, and the cardiomyocyte differentiation medium containing CHIR99021 was added. After culturing for 48 hours, the medium was replaced with cardiomyocyte differentiation medium containing IWR-1. After culturing for 48 hours, the culturing was continued with cardiomyocyte differentiation medium. The medium was replaced every 48 hours, and the cells were cultured until the beating was observable, then the contents of cardiomyocytes and fibroblasts were detected. The cardiomyocyte differentiation medium provided in the example of the present disclosure is RPMI1640 medium with B27 without insulin (RPMI1640 medium:B27 is 100:2). The cardiomyocyte culturing medium in the examples of the present disclosure may also be other medium that can differentiate pluripotent stem cells into cardiomyocytes.

When the final concentration of CHIR99021 is 0.01 to 0.09 mM and the final concentration of IWR is 0.01 to 0.05 mM, the differentiation efficiency of cardiomyocytes is relatively high. In order to further improve the differentiation efficiency of cardiomyocytes, 6 days after cardiomyocyte differentiation, pro-maturation factors such as insulin-containing B27 can be added. When the density of pluripotent stem cells exceeds 40%, it has no significant effect on the differentiation efficiency of cardiomyocytes. In order to lower the production costs, in the examples of the present disclosure, the step of cardiomyocyte differentiation may be performed when the culture density of pluripotent stem cells reaches 40%.

Step of cardiomyocyte purification: As the culture time of the cells in the cardiomyocyte differentiation medium extends, the content of pluripotent stem cells decreases, while the contents of cardiomyocytes and fibroblasts increase. In order to further control the content of fibroblasts, the cells prepared in the above steps need to be purified. The cells prepared in the above steps were digested with Accutase and centrifuged, the cardiomyocyte differentiation medium was added, and the cells were prepared into a cell suspension with a concentration of $6.0 \times 10^6$ to $9.0 \times 10^6$ cells/mL. The cells were seeded into a cell culture dish coated with Matrigel using cardiomyocyte differentiation medium at a density of $6.0 \times 10^5$ to $9.0 \times 10^5$ cells/cm$^2$, and then purified with cardiomyocyte purification liquid. Every 48 hours, the cardiomyocyte purification liquid was replaced, wherein the cardiomyocyte purification liquid is DMEM medium (no glucose) containing 1 µM cytosine β-D-arabinofuranoside and 0.02 M sodium lactate at a final concentration, respectively. With the extension of the purification time, the content of fibroblasts gradually decreases. When the content of fibroblasts meets the requirements of the cardiomyocyte formulation of the examples of the present disclosure, the purification can be terminated.

The above purification also includes, according to the content of pluripotent stem cells, culturing the cells prepared in the step of cardiomyocyte differentiation or the step of cardiomyocyte purification in a cardiomyocyte culture medium containing STF-31 at a concentration of 0.75-5 µM for 2-5 days. With the extension of the purification time in the cardiomyocyte culture medium containing STF-31, the content of pluripotent stem cells gradually decreases. The concentration of STF-31 and purification time can be selected according to actual needs.

The obtained cells were identified by immunofluorescence method. The above operations were all carried out under aseptic conditions.

Other methods for differentiating pluripotent stem cells into cardiomyocytes and methods for removing pluripotent stem cells or fibroblasts from cardiomyocytes known to those skilled in the art are also applicable to the present disclosure.

2) Preparation of Cardiomyocyte Formulation

In the examples of the present disclosure, the cells differentiated from pluripotent stem cells were formulated into cardiomyocyte formulations with different concentrations of cardiomyocytes using injection, and the specific method is as follows.

In the differentiation and purification steps of cardiomyocytes, the purity of cardiomyocytes, the purity of fibroblasts and the residual amount of pluripotent stem cells were tested. According to actual needs, control the parameters of the steps of cardiomyocyte differentiation and purification to adjust the contents of cardiomyocytes and fibroblasts, and minimize the number of residual pluripotent stem cells. In the examples of the present disclosure, flow cytometry was used to detect the contents of the above three types of cells.

Detection of cardiomyocyte purity: The cells to be tested were counted, fixed with 4% PFA, and prepared with DPBS to make 100 µL, of cell suspension with a concentration of $1 \times 10^7$ cells/ml. After the cells were centrifuged, 70 µL of 1% BSA and 20 µL of FCR Blocking Reagent were added and blocked at room temperature for 30 minutes. Then, 10 µL of Anti-Cardiac Troponin T-FITC was added, mixed and incubated at room temperature in the dark for 30 minutes. The cells were washed with DPBS and centrifuged, and then analyzed by flow cytometry. The control group was incubated with 80 µL of 1% BSA and 20 µL of FCR Blocking Reagent.

Detection of fibroblast purity: The cells to be tested were counted, fixed with 4% PFA, and prepared with DPBS to make 100 µL of cell suspension with a concentration of $1 \times 10^7$ cells/ml. After the cells were centrifuged, 75 µL of 1% BSA and 20 µL of FCR Blocking Reagent weer added and blocked at room temperature for 30 minutes. Then, 5 µL of Anti-human Vimentin Alexa 488 was added, mixed and incubated at room temperature in the dark for 30 minutes. The cells were washed with DPBS and centrifuged, and then analyzed by flow cytometry. The control group was incubated with 80 µL of 1% BSA and 20 µL of FCR Blocking Reagent.

Detection of residual pluripotent stem cells: The cells to be tested were counted, fixed with 4% PFA, and prepared with DPBS to make 100 µL of cell suspension with a concentration of $1 \times 10^7$ cells/ml. The cells were centrifuged and blocked and incubated with the following diluted antibodies: Anti-SSEA-4-PE, PE Mouse anti-human Nanog and PE Mouse anti-Oct3/4. Analysis was performed by using flow cytometry.

According to the step of cardiomyocyte purification provided in the present disclosure, the cardiomyocytes purified in the cardiomyocyte purification medium at day 7 had a purity of 71.49%, the purity of fibroblasts was 22.38%, and the residual amount of pluripotent stem cells was 4.2%. When the purification time of the cells in the cardiomyocyte purification medium was extended to 12 days, and then the purified cells were cultured in cardiomyocyte culture medium containing STF-31 at a concentration of 0.75-5 µM for 2 days, the detection results of the purity of cardiomyocytes, the purity of fibroblasts and the residual amount of pluripotent stem cells by flow cytometry showed that the purity of cardiomyocytes was 94.42%, the content of fibroblasts was 3.15%, and the residual amount of induced pluripotent stem cells was 0.53%.

The above cells were prepared into a cell suspension with injection-grade normal saline, and cardiomyocytes in the cell suspension were counted. By adjusting the amount of physiological saline added to control the concentration of cardiomyocytes in the cell suspension, a cell suspension with an appropriate concentration of cardiomyocytes was selected as the cardiomyocyte formulation.

In the example of the present disclosure, in addition to physiological saline as an injection, the following injections are also provided for the preparation of cardiomyocyte formulations:

(1) human serum albumin at a concentration of 5%;
(2) a mixed solution of DMSO, HAS, 15% glucose, dextran 40 glucose injection, and physiological saline in a volume ratio of 7.5:20:30:10:32.5.

The human albumin used in the example of the present disclosure was purchased from Baxter, DMSO was purchased from Sigma, HAS was purchased from Guizhou Bangtai, and dextran 40 glucose injection was purchased from Sichuan Kelun. No matter what solution is used in the cardiomyocyte formulation, cardiomyocytes are used as the main active ingredient of the formulation.

3. Cell Viability in Cardiomyocyte Formulations with Different Concentrations

Preparaton of cardiomyocyte formulation samples: The cells from the above differentiation steps were prepared into a cell suspension, and the content of cardiomyocytes, pluripotent stem cells and fibroblasts were detected. The samples with cardiomyocyte content higher than 80%, fibroblast content not higher than 20% and pluripotent stem cell residual content not higher than 1% was prepared according to the number of cardiomyocytes using physiological saline under aseptic conditions into cardiomyocyte formulations with the following cardiomyocyte concentrations (cells/mL): $0.5 \times 10^7$, $0.75 \times 10^7$, $0.3 \times 10^8$, $0.5 \times 10^8$, $1.2 \times 10^7$, $0.75 \times 10^9$, $1.0 \times 10^9$ and $3.0 \times 10^9$.

Determination of Cell Viability

Each 5 mL of the above cardiomyocyte formulation was stained with 0.2% trypan blue, and then the cell viability was measured by Countstar. The cardiomyocyte formulations with different concentrations were stored in a refrigerator at 4° C. for 4 hours and then the cell viability was measured by the same method. The results are shown in Table 1.

Echocardiography is a non-invasive method of evaluating heart function, which can dynamically observe animal heart function. In the example of the present disclosure, left ventricular end-systolic diameter (LVESD), left ventricular end-systolic volume (LVESV), and thickness of left ventricular anterior wall (LVAW), left ventricular ejection fraction (EF), and left ventricular short-axis fractional shortening (FS) are selected as indicators of cardiac function evaluation.

The rats after coronary artery ligation were housed for 2-6 weeks, and their left ventricular ejection fraction (EF) was measured by echocardiography. Rats with EF<40% meet the selection criteria of the experiment and can be used as a successful heart failure model.

2) Results of Different Concentrations of Cardiomyocyte Formulation on Improving Cardiac Function The cardiomyocyte formulations described in the present disclosure are preferably prepared from pluripotent stem cells of allogeneic origin according to the subject of heart failure. Studies have found that under the premise of injecting the same number of cardiomyocytes in a heart failure model, the degree of improvement in cardiac function varies with the concentration of cardiomyocytes in the cardiomyocyte formulation. In order to further understand the influence of the concentration of cardiomyocytes on the therapeutic

TABLE 1

Effect of cardiomyocyte concentration on cell viability

| | cardiomyocyte concentration (cells/mL) | | | | | | | |
|---|---|---|---|---|---|---|---|---|
| | $0.5 \times 10^7$ | $0.75 \times 10^7$ | $0.3 \times 10^8$ | $0.5 \times 10^8$ | $1.2 \times 10^7$ | $0.75 \times 10^9$ | $1.0 \times 10^9$ | $3.0 \times 10^9$ |
| cell viability (refrigerated 0 h) | 98.74% | 99.06% | 98.15% | 97.64% | 98.56% | 99.17% | 98.39% | 97.06% |
| cell viability (refrigerated 4 h) | 91.75% | 92.89% | 89.51% | 86.09% | 85.47% | 83.69% | 78.31% | 61.96% |

Table 1 shows the cell viability of the prepared cardiomyocyte formulations with different concentrations and the cell viability of the cardiomyocyte formulations with different concentrations stored at 4° C. for 4 hours. As shown in Table 1, the concentration of cardiomyocytes affects the cell viability. The higher the concentration, the more the cell viability decreases. According to the cell viability of the cardiomyocyte formulation at 4 h, and considering the process from preparation to use of the cardiomyocyte formulation, the concentration of cardiomyocytes should be below $1.0 \times 10^9$ to avoid the loss of cardiomyocytes.

2. Animal Experiments

1) Establishment of Rat Heart Failure Model

The principle of establishing a rat model of heart failure after myocardial infarction is that, by causing the rat myocardial necrosis, ventricular wall motion and compliance are weakened, and the heart function is transformed from compensation to decompensation and eventually heart failure. At present, the most widely used method is coronary artery ligation, in which if the ligation position is too high, it is easy to cause the death of the rat, and if the ligation position is too low, the infarct area may be too small.

The example of the present disclosure establishes a heart failure model through the following operations: after the rat was anesthetized, it were connected to a small animal ventilator via an oral cannula, the chest was opened, and the left anterior descending coronary artery was ligated. After the operation, the rat was injected with 160 IU/kg of penicillin via the intraperitoneal cavity every day for 3 to 5 days.

effect, the cardiomyocyte formulations shown in Table 2 (the cardiomyocyte formulations prepared from physiological saline described above) were selected and injected into a scar area or a thinned myocardial wall region through the epicardium of the rat. After the injection, the rats were given 15 mg/kg cyclosporine A and 2 mg/kg methylprednisolone by gavage every day to prevent immune rejection, and the recovery of heart function of the heart failure model was observed by echocardiography.

In the example of the present disclosure, the cardiomyocyte formulation can be differentiated from induced pluripotent stem cells or embryonic stem cells. The cardiomyocyte formulations from the two sources showed no significant difference in the improvement of heart function in heart failure model. The following experiments used cardiomyocyte formulation differentiated from induced pluripotent stem cells.

TABLE 2

Effect of different cardiomyocyte formulations on change of ejection fraction in heart failure model

| example No. | cardiomyocyte concentration (cells/mL) | fibroblast content | change of ejection fraction |
|---|---|---|---|
| 1 | $0.4 \times 10^7$ | 10% | 3.17% |
| 2 | $0.5 \times 10^7$ | 10% | 5.43% |
| 3 | $0.75 \times 10^7$ | 10% | 8.31% |

TABLE 2-continued

Effect of different cardiomyocyte formulations on
change of ejection fraction in heart failure model

| example No. | cardiomyocyte concentration (cells/mL) | fibroblast content | change of ejection fraction |
|---|---|---|---|
| 4 | $0.3 \times 10^8$ | 10% | 14.92% |
| 5 | $0.5 \times 10^8$ | 10% | 17.11% |
| 6 | $1.2 \times 10^8$ | 5% | 13.26% |
| 7 | $1.2 \times 10^8$ | 10% | 22.99% |
| 8 | $1.2 \times 10^8$ | 20% | 19.27% |
| 9 | $1.2 \times 10^8$ | 25% | 8.68% |
| 10 | $1.2 \times 10^8$ | 30% | 5.25% |
| 11 | $0.75 \times 10^9$ | 10% | 13.01% |
| 12 | $1.0 \times 10^9$ | 10% | 6.9% |

Wherein, the control group was injected with the same dose of normal saline as the experimental groups (examples 1-12) in heart failure model rats via the same injection method, and anti-immune rejection drugs were given in the same manner. The control group and the experimental groups were simultaneously subjected to echocardiography to observe various parameters reflecting heart function. In the example of the present disclosure, the change of ejection fraction is the difference between the ejection fraction at D28 and D0.

The total amount of injected cells in each experimental group was the same, and the appropriate injection dose was decided according to the concentration of cardiomyocytes in each group. For example, if the total number of cells injected in each example was $1.2 \times 10^6$ cells, and the concentration of cardiomyocytes in example 6 was $1.2 \times 10^8$ cells/mL, then rats in example 6 were injected with 10 μl of cardiomyocyte formulation to reach a total injection amount of $1.2 \times 10^6$ cells.

The change of ejection fraction in Table 2 is the difference between the ejection fraction 28 days after the injection of the cardiomyocyte formulation and the ejection fraction before the injection of the experimental group with a total injection amount of $1.2 \times 10^7$ cardiomyocytes. FIG. 1 shows that the left ventricular anterior wall became thinner in the control group with time, and the left ventricular diameter and left ventricular volume both increased to a certain extent with time, indicating the decline of heart function. The heart function of the experimental group on D28 was better than that of the control group on D28. These results demonstrate that the cardiomyocyte formulation provided by the present disclosure can effectively reduce the degree of cardiac function decline.

Figure 2A:
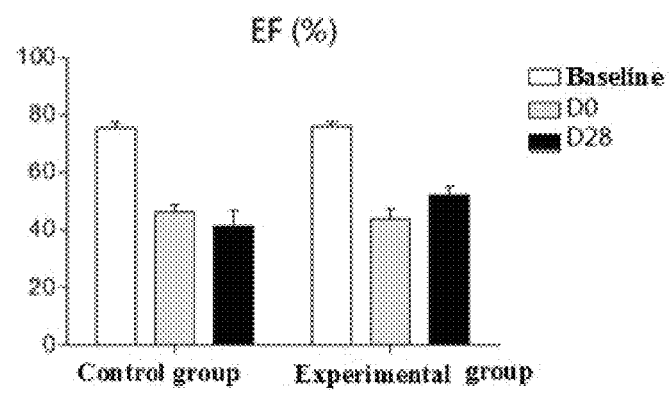
FIG. 2A shows the ejection fraction of the control group and the experimental group of Example 3 before the establishment of the heart failure model (baseline), D0 and D28, respectively.
Figure 2B:
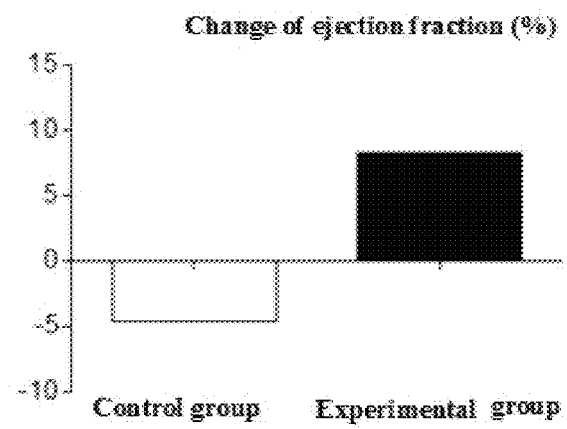
FIG. 2B shows the change in ejection fraction of the experimental group and the control group at D28 relative to D0, wherein the ejection fraction of D28 in the experimental group increased relative to D0, and the change of ejection fraction was 8.31%.
Figure 3:
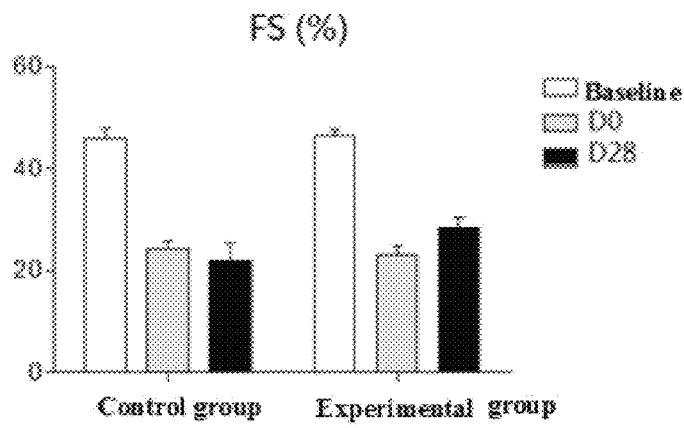
FIG. 3 shows the left ventricular short-axis fractional shortening of the control group and the experimental group of Example 3 before the establishment of the heart failure model (baseline), D0 and D28, respectively. The experimental group had an increased left ventricular short-axis fractional shortening compared with the control group at D28.
Figure 6:
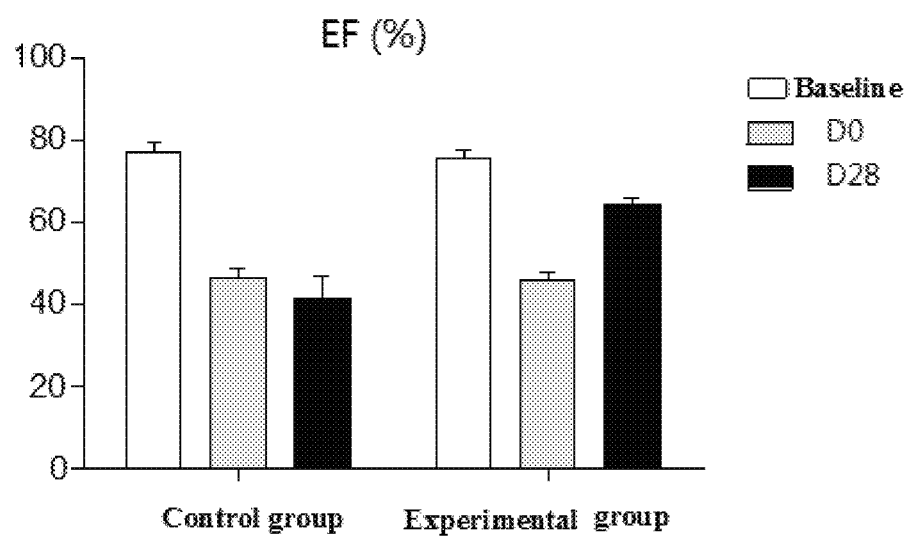
FIG. 6 shows the ejection fraction of the control group and the experimental group of Example 7 before the establishment of the heart failure model (baseline), D0 and D28, respectively. The ejection fraction of the control group decreased at D28 relative to D0, while the ejection fraction of the experimental group increased at D28 relative to D0, and the ejection fraction changed by 22.99%.

FIGS. 2 and 6 show the effects of cardiomyocyte formulations of example 3 and example 7 on ejection fraction in Table 2, respectively. Table 2 shows that cardiomyocyte formulations at different concentrations have different degrees of improvement on cardiac function. Among them, example 7 cardiomyocyte formulation, which has a cardiomyocyte concentration of $1.2 \times 10^8$ cells/mL and a fibroblast content of 10%, shows the best effect on improving ejection fraction. FIG. 3 shows that the left ventricular short-axis fractional shortening of the control group decreased with time, while the left ventricular short-axis fractional shortening of the experimental group 28 days after the injection of cardiomyocytes was higher than that before the injection, indicating that the injection of cardiomyocyte formulations restored heart function.

Figure 4A:
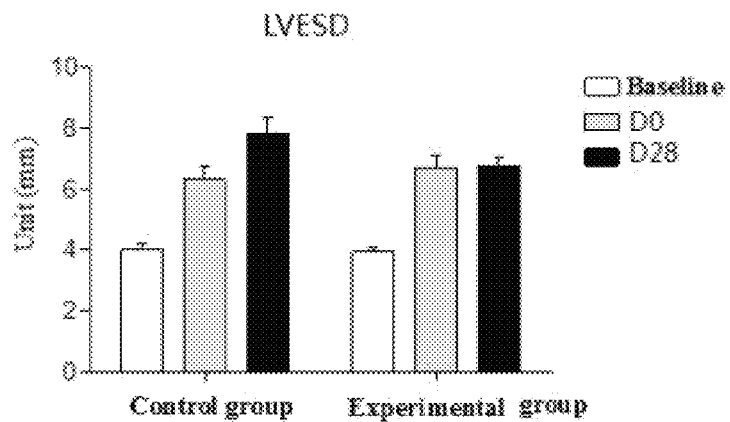
FIG. 4A shows the left ventricular end-systolic diameter of the control group and the experimental group of Example 3 before the establishment of the heart failure model (baseline), D0 and D28, respectively.
Figure 4B:
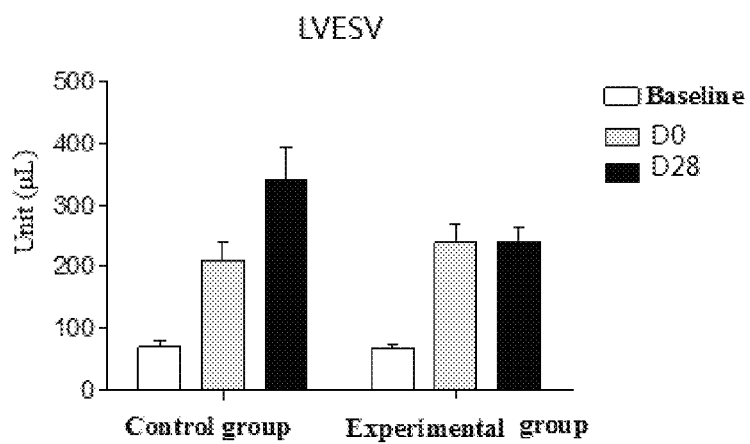
FIG. 4B shows the left ventricular end-systolic volume of the control group and the experimental group of Example 3 before the establishment of the heart failure model (baseline), D0 and D28, respectively. The left ventricular end-systolic diameter and left ventricular systolic volume of the experimental group did not continue to increase from D0 to D28 compared to the control group, and the degree of heart failure was suppressed.
Figure 5:
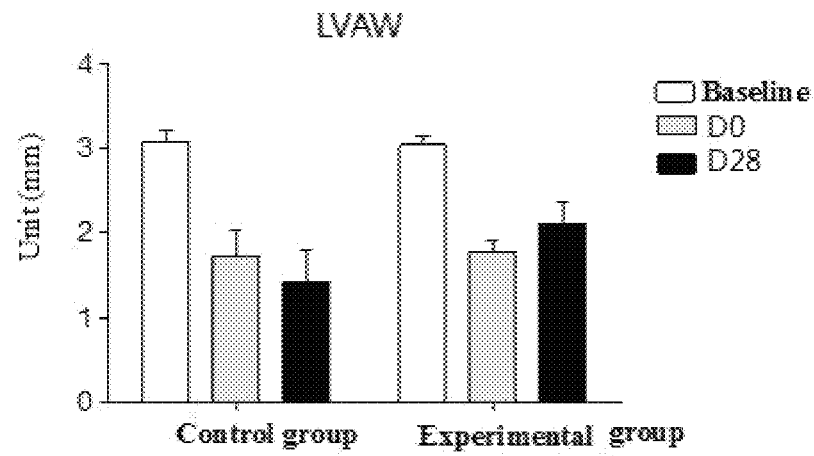
FIG. 5 shows the anterior wall thickness of left ventricle end-systole of the control group and the experimental group of Example 3 before the establishment of the heart failure model (baseline), D0 and D28, respectively. The anterior wall thickness of left ventricle end-systole in the control group was thinner at D28 relative to D0, while the anterior wall thickness of left ventricle end-systole in the experimental group increases at D28 relative to D0.

FIGS. 4 and 5 respectively show that in the heart failure model without cell therapy. As the extension of time, the left ventricular end-systolic diameter and left ventricular end-systolic volume became larger, and the left ventricular anterior wall thickness became thinner at the end-systole. In the experimental group, after 28 days of treatment with cardiomyocyte formulation, the left ventricular end-systolic diameter and left ventricular end-systolic volume did not continue to increase, and the thickness of the left ventricular anterior wall at the end-systolic period increased to a certain extent after cell therapy. Therefore, according to various indicators for evaluating cardiac function, it can be concluded that the cardiomyocyte formulations can increase myocardial contractility to a certain extent, increase ventricular wall tension, and improve cardiac function.

In the example of the present disclosure, when the total number of cardiomyocytes was $7.5 \times 10^6$ or $2.0 \times 10^8$ for the heart failure model, the effects of the cardiomyocyte concentrations on the cardiac function were also studied. Under the premise that the total amount of injection for each heart failure model in each group of experiments was determined (the groups injected with the same total amount of cardiomyocytes were grouped), the injection method of cardiomyocyte formulation can be one injection or multiple injections. The results of multiple groups of experiments showed that the concentration of cardiomyocytes affects the degree of improvement of heart function. In different groups of experiments, the degree of improvement of cardiac function along with the concentration change of cardiomyocytes was consistent with the results of the cardiomyocyte experimental group injected with a total of $1.2 \times 10^7$ cardiomyocytes. In the actual treatment of heart failure, it is necessary to select a suitable injection dose and a cardiomyocyte formulation with a suitable concentration of cardiomyocytes according to the subjects with heart failure and the severity of the heart failure.

Tumorigenicity Test of Cardiomyocyte Formulations

Tumorigenicity refers to the process by which the inoculated cells form tumors in the animal body after the animal is inoculated with cells. In the example of the present disclosure, the tumorigenicity test in nude mice and the soft agar cloning test were used to evaluate the tumorigenicity of the cardiomyocyte formulations. In the example of the present disclosure, the tumorigenicity of cardiomyocyte formulations derived from induced pluripotent stem cells and cardiomyocyte formulations derived from embryonic stem cells were studied, respectively, in which Hela cells were used as a positive control. The parameters of the tumorigenicity test samples are shown in Table 3 and Table 4.

TABLE 3

Sample parameters of cardiomyocyte formulations derived
from induced pluripotent stem cells for tumorigenicity test

| example No. | cardiomyocyte concentration (cells/mL) | residual amount of pluripotent stem cells |
|---|---|---|
| 13 | $0.3 \times 10^8$ | 30% |
| 14 | $0.3 \times 10^8$ | 10% |
| 15 | $0.3 \times 10^8$ | 3% |
| 16 | $0.3 \times 10^8$ | 1% |
| 17 | $0.3 \times 10^8$ | 0.5% |
| 18 | $1.2 \times 10^8$ | 30% |
| 19 | $1.2 \times 10^8$ | 10% |
| 20 | $1.2 \times 10^8$ | 3% |
| 21 | $1.2 \times 10^8$ | 1% |
| 22 | $1.2 \times 10^8$ | 0.5% |
| 23 | $0.75 \times 10^9$ | 30% |
| 24 | $0.75 \times 10^9$ | 10% |
| 25 | $0.75 \times 10^9$ | 3% |

TABLE 3-continued

Sample parameters of cardiomyocyte formulations derived from induced pluripotent stem cells for tumorigenicity test

| example No. | cardiomyocyte concentration (cells/mL) | residual amount of pluripotent stem cells |
|---|---|---|
| 26 | $0.75 \times 10^9$ | 1% |
| 27 | $0.75 \times 10^9$ | 0.5% |

Residual pluripotent stem cells in cardiomyocyte formulations derived from embryonic stem cells may also be tumorigenic. Table 4 lists the tumorigenicity test samples with different pluripotent stem cells residual amounts in the cardiomyocyte formulations.

TABLE 4

Sample parameters of cardiomyocyte formulations derived from embryonic stem cells for tumorigenicity test

| example No. | cardiomyocyte concentration (cells/mL) | residual amount of pluripotent stem cells |
|---|---|---|
| 28 | $1.2 \times 10^8$ | 50% |
| 29 | $1.2 \times 10^8$ | 30% |
| 30 | $1.2 \times 10^8$ | 10% |
| 31 | $1.2 \times 10^8$ | 1.0% |
| 32 | $1.2 \times 10^8$ | 0.5% |
| 33 | $1.2 \times 10^8$ | 0.3% |

The content of fibroblasts in the cardiomyocyte formulations of the above groups were all 10%.

1. Tumor Formation Experiment in Nude Mice

Nude mice were randomly divided into test group, blank control group and positive control group. The formulation samples listed in Table 3 and Table 4 were used as the test group, physiological saline was used as the blank control group, and Hela cells with a concentration of $1.8 \times 10^6$ cells/mL were used as positive control. The cells were inoculated subcutaneously on the back of nude mice, the inoculation volume was all 0.2 mL, and each sample was subjected to 5 parallel experiments, and the situation of the inoculation site of nude mice was regularly observed.

The results showed that there was no tumor formation in the blank control group, examples 13-22 and examples 24-33 within six months after inoculation, no nodules were formed at the inoculation site, and the tumor formation rate was 0. In the five parallel experiments of example 23, one of the nude mice had small and tough nodules at the inoculation site on the 28th day of inoculation. Two months after the inoculation, obvious lumps were seen on the back of the nude mouse, and the tumor formation rate of this cardiomyocyte formulation was 1/5.

2. Soft Agar Colony Formation Assay 1.2% agarose and pluripotent stem cell culture medium were mixed at a ratio of 1:1, 5 mL mixture was added to a 6 cm culture dish as the bottom agar, and 0.5% agarose and pluripotent stem cell culture medium were mixed at a ratio of 1:1 as the upper agar. The cardiomyocyte formulations of examples 13 to 33 were counted and tested for viable cells. 1 mL of cardiomyocyte formulations of examples 13 to 33 were added to 5 mL of the upper agar and slowly poured into the culture dish. Blank control was set, and Hela cells with a concentration of $1.8 \times 10^6$ cells/mL were set as positive control. The double-layer soft agar dishes were placed in a 37° C., 5% $CO_2$ incubator for 30 days. The dishes were put under a microscope to observe the formation of cell colony, and the rate of cell colony formation was calculated.

Rate of cell colony formation=(number of cell colony/total cell number in a dish)×100%

The soft agar cell colony formation assay is a commonly used experimental method to detect the growth potential of cell colonies in vitro, in which the in vivo extracellular matrix is simulated by the semi-solid growth environment. Tumor cells can proliferate indefinitely and show strong colony forming ability, while mature and differentiated cells cannot form colonies. According to this feature, in the example of the present disclosure, the tumorigenicity of the cardiomyocyte formulations were evaluated by comparing the colony formation rates of the cardiomyocyte formulations with different pluripotent stem cell residual amounts.

The cell colony formation rate in the positive control group was 5.1%, while the blank control group and examples 16, 17, 21, 22, 26, 27, 31, 32, and 33 had no colony formation. The remaining examples had different numbers of cell colonies, and the cell colony formation rate increased with the increase of the residual amount of pluripotent stem cells.

Based on the results of nude mice tumor formation experiments and soft agar colony formation experiments, the residual amount of pluripotent stem cells in the cardiomyocyte formulations should be controlled within 1% to ensure the safety of the cardiomyocyte formulations.

It should be noted that the above examples are only used to further illustrate the present disclosure, but the implementation of the present disclosure is not restricted by the above examples. Other changes, modifications, substitutions, and combinations made on the basis of the present disclosure that are essentially the same as those of the present disclosure shall be regarded as equivalent replacement means, and shall be included in the protection scope of the present disclosure.

The invention claimed is:

1. A cardiomyocyte formulation comprising cardiomyocytes and fibroblasts differentiated from pluripotent stem cells, wherein the concentration of the cardiomyocytes in the cardiomyocyte formulation is $0.75 \times 10^7$ to $1.2 \times 10^8$ cells/mL, and the content of the cardiomyocytes is higher than 80% and the content of the fibroblasts is not higher than 20%.

2. The cardiomyocyte formulation of claim 1, wherein residual amount of the pluripotent stem cells in the cardiomyocyte formulation is not more than 1%.

3. The cardiomyocyte formulation of claim 2, wherein residual amount of the pluripotent stem cells in the cardiomyocyte formulation is not higher than 0.3%.

4. A method for preparing the cardiomyocyte formulation of claim 1, wherein the cardiomyocytes are prepared from pluripotent stem cells by steps of:
   1) Pretreating the pluripotent stem cells: seeding the pluripotent stem cells into a pluripotent stem cell culture medium at a density of $0.9 \times 10^5$ to $3.0 \times 10^5$ cells/cm$^2$, culturing the cells at 37° C. with 5% $CO_2$ until cell density exceeds 40%;
   2) differentiating to cardiomyocytes: removing the pluripotent stem cell culture medium by suction, adding cardiomyocyte differentiation medium containing 0.01 to 0.09 mM CHIR99021, culturing for 48 hours; replacing the medium with cardiomyocyte differentiation medium containing 0.01 to 0.05 mM IWR-1, continuing to culture the cells for 48 hours; continuing to culturing with the cardiomyocyte differentiation medium, and replacing the cardiomyocyte differentiation medium according to cell growth state; and
   3) Purifying cardiomyocytes: continuing to culture the cardiomyocytes via the step of differentiating to cardiomyocytes until emergence of observable beating, seeding the cells in the cardiomyocyte differentiation medium at a density of $6.0 \times 10^5$ to $9.0 \times 10^5$ cells/cm$^2$, and adjusting the content of fibroblasts to less than 20% by using a cardiomyocyte purification liquid.

5. The method for preparing the cardiomyocyte formulation of claim 4, wherein the pluripotent stem cells include induced pluripotent stem cells and embryonic stem cells.

6. The method for preparing the cardiomyocyte formulation of claim 4, wherein the step of purifying cardiomyocytes further comprises culturing the cells in a cardiomyocyte culturing medium containing 0.75-5 µM STF-31 for 2-5 days.

7. The method for preparing the cardiomyocyte formulation of claim 4, further comprising preparing a cell suspension with a cardiomyocyte concentration of $0.75 \times 10^7$ to $1.2 \times 10^8$ cells/mL by using the cells obtained in the step of purifying cardiomyocytes and physiological saline under sterile conditions.

8. A method of treating heart failure, comprising administering the cardiomyocyte formulation of claim 1 to a subject in need thereof.

9. The method according to claim 8, wherein the cardiomyocyte formulation is used to treat heart failure with reduced ejection fraction (HFrEF).

10. The method according to claim 8, wherein the cardiomyocyte formulation is injected through epicardium via a syringe into a scar or a thinned myocardial wall region.

* * * * *